United States Patent
Wittnebel et al.

(10) Patent No.: US 10,420,677 B2
(45) Date of Patent: Sep. 24, 2019

(54) SYSTEM AND METHOD FOR INDIRECTLY DETERMINING WEIGHT ON EYE DURING LASER OPHTHALMIC SURGERY

(71) Applicant: Novartis AG, Basel (CH)

(72) Inventors: Michael Wittnebel, Hirschaid (DE); Martin Starigk, Nuremberg (DE)

(73) Assignee: Novartis AG (CH)

( * ) Notice: Subject to any disclaimer, the term of this patent is extended or adjusted under 35 U.S.C. 154(b) by 93 days.

(21) Appl. No.: 15/561,461

(22) PCT Filed: Nov. 3, 2016

(86) PCT No.: PCT/IB2016/056628
§ 371 (c)(1),
(2) Date: Sep. 25, 2017

(87) PCT Pub. No.: WO2018/083520
PCT Pub. Date: May 11, 2018

(65) Prior Publication Data
US 2018/0256392 A1    Sep. 13, 2018

(51) Int. Cl.
*A61F 9/009* (2006.01)
*A61F 9/008* (2006.01)

(52) U.S. Cl.
CPC .......... *A61F 9/009* (2013.01); *A61F 9/00825* (2013.01); *A61F 2009/00863* (2013.01); *A61F 2009/00887* (2013.01)

(58) Field of Classification Search
CPC ................ A61F 9/009; A61F 9/00825; A61F 2009/00863; A61F 2009/00887
See application file for complete search history.

(56) References Cited

U.S. PATENT DOCUMENTS

| | | | | |
|---|---|---|---|---|
| 2008/0243107 A1* | 10/2008 | Muhlhoff | ............ | A61F 9/00825 606/4 |
| 2010/0256614 A1* | 10/2010 | Donitzky | ................ | A61F 9/008 606/4 |
| 2010/0280509 A1* | 11/2010 | Muller | ................... | A61B 18/18 606/33 |
| 2011/0009851 A1* | 1/2011 | Donitzky | ............ | A61F 9/00825 606/4 |
| 2011/0190741 A1* | 8/2011 | Deisinger | ........... | A61F 9/00827 606/5 |

(Continued)

FOREIGN PATENT DOCUMENTS

EP         2913036 A1      9/2015

*Primary Examiner* — Eric F Winakur
*Assistant Examiner* — Abid A Mustansir
(74) *Attorney, Agent, or Firm* — Keiko Ichiye, Esq.

(57) ABSTRACT

The present disclosure provides a system and method for indirectly determining weight on eye, the weight resulting from contact between the eye and a docking apparatus for laser ophthalmic surgery. The system includes a docking apparatus, a measuring device, a display and a processor that determines a relative distance between a detectable position of a component of the docking apparatus and a neutral position of the eye, determines the weight on eye by reference to sensed force-distance reference data, and generates and transmits a pictorial representation of weight on eye to a display. The disclosure further provides a method for indirectly determining weight on eye, the weight resulting from contact between the eye and a docking apparatus for laser ophthalmic surgery.

18 Claims, 5 Drawing Sheets

(56) References Cited

U.S. PATENT DOCUMENTS

2012/0240939 A1    9/2012  Kandulla
2014/0128852 A1    5/2014  Gooding et al.
2015/0335479 A1*  11/2015  Shibata ............... A61F 9/00825
                                                        606/5

* cited by examiner

SYSTEM AND METHOD FOR INDIRECTLY DETERMINING WEIGHT ON EYE DURING LASER OPHTHALMIC SURGERY

CROSS REFERENCE TO RELATED APPLICATIONS

This application is a section 371 national stage phase of International Application No. PCT/IB2016/056628, filed 3 Nov. 2016, titled "SYSTEM AND METHOD FOR INDIRECTLY DETERMINING WEIGHT ON EYE DURING LASER OPHTHALMIC SURGERY," which is hereby incorporated by reference in its entirety.

TECHNICAL FIELD

The present disclosure relates to ophthalmic surgery and surgical equipment, and more specifically, to systems and methods for indirectly determining weight on eye during laser ophthalmic surgery.

BACKGROUND

Ophthalmic surgery saves and improves the vision of tens of thousands of patients every year. However, given the sensitivity of vision to even small changes in the eye and the minute and delicate nature of many eye structures, ophthalmic surgery is difficult to perform and the reduction of even minor or uncommon surgical errors or modest improvements in accuracy of surgical techniques can make an enormous difference in the patient's vision after the surgery.

Ophthalmic surgery is surgery performed on the eye or any part of the eye. Ophthalmic surgery is regularly performed to repair retinal defects, repair eye muscles, remove cataracts or cancer, or to restore or improve vision. Refractive eye surgery, for example, is a type of ophthalmic surgery used to improve the refractive state of the eye for the purpose of decreasing or eliminating dependency on glasses or contact lenses. Refractive surgery procedures may include surgically remodeling the cornea and/or cataract surgery, either of which may be performed by lasers.

In various ophthalmic surgical procedures, a laser uses photodisruption to create incisions. When performing ophthalmic surgery with lasers, a surgical procedure typically includes docking, imaging, analysis, and laser treatment. During docking, a patient's eye is docked to a suction cone in order to provide pressure to flatten the patient's cornea (known as applanation) and hold it in position for the laser treatment. Docking is a sensitive process, and proper placement of the suction cone in the Z-direction, and in the X and Y-directions, is important for successful ophthalmic surgery. Upon contact with the eye and during docking various forces are applied to the eye and it is important to discern whether such forces are excessive or capable of damaging the eye tissue, causing inflammation, or causing other potentially avoidable complications.

SUMMARY

The present disclosure provides a system for indirectly determining weight on eye during laser ophthalmic surgery. The system includes a docking apparatus, a measuring device operable to detect a detectable position of a component of the docking apparatus and generate data relating to the detectable position, a display, and a processor operable to receive data from the measuring device relating to the detectable position, determine a relative distance between the detectable position of the component in relation to a neutral position of the eye, determine weight on eye resulting from contact between the docking apparatus and the eye by reference to sensed force-distance reference data, generate a pictorial representation of the weight on the in eye in relation to the detectable position, and transmit the pictorial representation to the display.

In additional embodiments, which may be combined with one another unless clearly exclusive: the system further comprises incorporating a force sensor into the system or a functionally identical system, the force sensor operable to sense a sensed force and generate data relating to the sensed forced that corresponds to weight on eye, receiving at the processor, data from the force sensor and the measuring device, and correlating weight on eye to the relative distance to generate the sensed force-distance reference data distance reference data; the weight on eye is determined by extrapolating the sensed force-distance reference data; the sensed force-distance reference data is extrapolated to include any detectable position in an entire range of motion of the component, or any subset thereof the components of the docking apparatus include a suction cone, a suction ring, and a lens; the components of the docking apparatus include a suction cone, a control device operable to adjust the position of the suction cone, a suction ring, and a lens; the measuring device is operable to detect a detectable position of the suction cone by using light barriers, switches, a path recorder, an eye camera, multiple eye cameras, or an eye tracking system; the neutral position of the eye is a position in which the eye is in contact with the component and the eye are in contact, with a substantially neutral pulling or pushing force on the eye based on the contact; the force sensor is a weighing device; the processor is further configured to generate a warning and transmit the warning to the display, the warning indicating that the weight on eye is outside of a defined acceptable range; and the warning further indicates that adjustment of the component of the docking apparatus is necessary, the direction the component must be adjusted to remain in the defined acceptable range, the extent to which the component must be adjusted in the Z-direction, or any combination thereof.

The present disclosure further provides a method for maintaining the position of a suction cone on an eye during laser ophthalmic surgery. The method includes receiving data from a measuring device relating to a detectable position of a component of a docking apparatus, determining a relative distance between the detectable position of the component in relation to a neutral position of the eye, determining the weight on eye resulting from contact between the docking apparatus and the eye by reference to sensed force-distance reference data, generating a pictorial representation of weight on the in eye in relation to the detectable position, and transmitting the pictorial representation to a display.

In additional embodiments, which may be combined with one another unless clearly exclusive: the sensed force-distance reference data is generated by receiving at the processor data relating to the sensed forced that corresponds to weight on eye and data relating to a detectable position, and correlating weight on eye to the relative distance to generate the sensed force-distance reference data distance reference data; the weight on eye is determined by extrapolating the sensed force-distance reference data; the sensed force-distance reference data is extrapolated to include any detectable position within an entire range of motion of the component, or any subset thereof the neutral position of the eye is a position in which the eye is in contact with the component, with a substantially neutral pulling or pushing force on the eye based on the contact; determining the weight on eye by reference to sensed force-distance reference data further includes generating and transmitting a warning, the warning indicating that the weight on eye is outside of a defined weight measurement range; and the warning further indicates that adjustment of the component of the docking apparatus is necessary, the direction the component must be adjusted to remain in the defined acceptable range, the extent to which the component must be adjusted in the Z-direction, or any combination thereof.

The above systems may be used with the above methods and vice versa. In addition, any system described herein may be used with any method described herein and vice versa.

BRIEF DESCRIPTION OF THE DRAWINGS

For a more complete understanding of the present invention and its features and advantages, reference is now made to the following description, taken in conjunction with the accompanying drawings, which are not to scale, in which like numerals refer to like features, and in which.

DETAILED DESCRIPTION

In the following description, details are set forth by way of example to facilitate discussion of the disclosed subject matter. It should be apparent to a person of ordinary skill in the field, however, that the disclosed embodiments are exemplary and not exhaustive of all possible embodiments.

The present disclosure provides systems and methods for indirectly determining weight on eye during laser ophthalmic surgery. Throughout this disclosure, movement may be described with respect to the eye undergoing surgery. Movement in an X-direction or Y-direction occurs in an X-Y plane perpendicular to the apex of the eye. Movement in a Z-direction occurs in a direction perpendicular to the X-Y plane. In the present disclosure, "lower," "down" and "downwards" in the Z-direction refer to movement or a position closer to the patient's eye. "Higher," "up" and "upwards" in the Z-direction refer to movement or a position further away from the patient's eye.

At the beginning of an ophthalmic surgical procedure, a patient is typically placed on a support facing upward toward the ceiling, which may be, for example, a couch or a bed. Before the laser surgical procedure can begin, components of a docking apparatus must be docked to the eye. Typically, these components include a suction ring, a suction cone, and a lens. The suction cone and lens are typically part of a femtosecond laser. Often the suction ring is positioned on the eye manually, although it may also be positioned via a control device. A suction cone may then be lowered manually or via a control device until it is in contact with the eye and proper suction may be achieved through the use of a first and second vacuum. When the suction cone contacts the eye, contact between the lens and the eye causes applanation, a flattening of the surface of the eye. Next, the suction cone may be raised to an optimal working range. The femtosecond laser applies a pushing force on the eye downwards in the Z-direction. During adjustment of suction cone's position, this pushing force may increase, causing greater weight on eye. If the suction cone is very near the eye and movement in the Z-direction continues downward, a pulling effect may occur, which may also affect weight on eye.

The application of either a pushing force or a pulling force on the eye may cause a significant change in intraocular eye pressure and other parameters vital to a successful surgical procedure. One significant measure of pushing forces or pulling forces is weight on eye. In general, weight on eye is affected by any pushing or pulling forces on the eye, particularly by the femtosecond laser, but weight on eye does not tend to linearly correlate with pushing or pulling forces. Because an excessive weight on eye may damage the eye tissue itself or lead to other complications, inflammation, or unintended side effects, it is important to determine the weight on eye resulting from contact between the docking apparatus and the eye, including effects of forces applied by the femtosecond laser. Additionally, it is useful to monitor any changes in the weight on eye during a surgical procedure in case the weight on eye becomes excessive. The present disclosure provides an indirect method of determining weight on eye during a surgical procedure using the position of the docking apparatus in the Z-direction.

Figure 1:
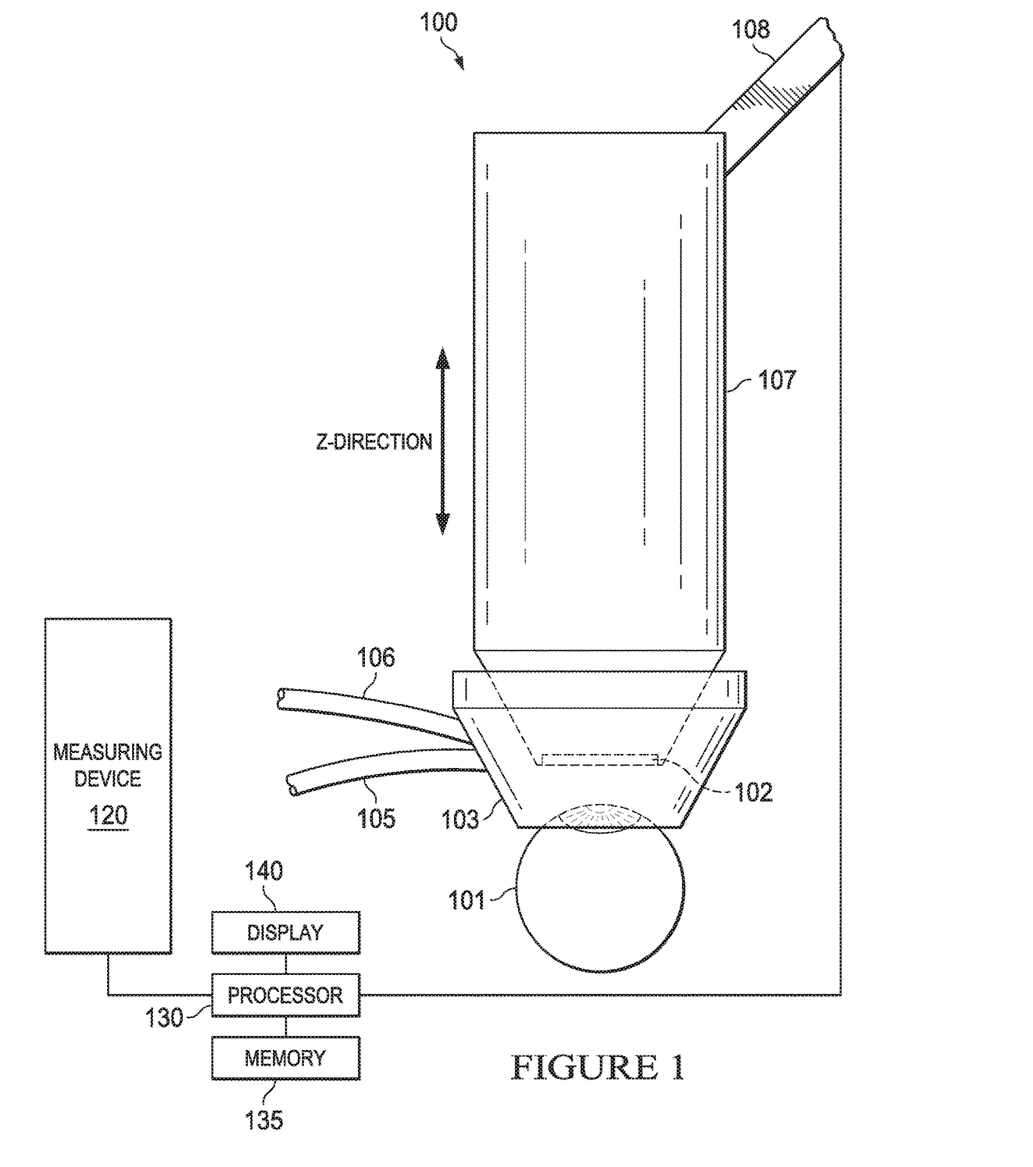
FIG. 1 is a schematic representation of a system for indirectly determining weight on eye during laser ophthalmic surgery.

Referring now to the figures, FIG. 1 is a schematic representation of a system for indirectly determining weight on eye during laser ophthalmic surgery, the system in an un-docked state. The system is in an un-docked state because the docking apparatus has not been successfully docked to the eye, as indicated by a lack of contact between lens 102 and eye 101. As shown, the docking apparatus of system 100 includes a suction ring 103, connected to a first vacuum 105 and a second vacuum 106, lens 102, and suction cone 107, connected to control device 108, which is operable to adjust the position of the suction cone in the Z-direction. System 100 further includes processor 130, which is connected to memory 135, control device 108, measuring device 120, and display 140. Any of the electronic components of system 100 may be connected through a cable-connected or wireless connection.

As shown in FIG. 1, suction ring 103 has been positioned on eye 101. Suction cone 107 may now be docked to the eye by lowering it in the Z-direction via control device 108. When suction cone 107 is lowered such that lens 102 contacts the eye, a pushing force is applied to the eye, the pushing force resulting from contact between the docking apparatus and the eye. A pulling force is also applied to the eye, the pulling force resulting from suction generated by vacuums 105 and 106.

Later, a femtosecond laser (not shown) is coupled with docking apparatus, resulting in a much greater pushing force on the eye transmitted through the docking apparatus. The position of the laser may be adjusted, which results in movements of the docking apparatus that may increase or decrease weight on eye.

Measuring device 120 is operable to detect a detectable position of the suction cone and generate data relating to the detectable position. For example, measuring device 120 may be operable to detect a detectable position of the suction cone by using light barriers, switches, a path recorder, an eye camera, multiple eye cameras, or an eye tracking system. Processor 130 is operable to receive data from the measuring device and determine a relative distance between the detectable position of the suction cone in relation to a defined "neutral position." The "neutral position," defined by the user, indicates a neutral position of the eye, which is a position in which the eye is in contact with the component (of the docking apparatus), with a substantially neutral pulling or pushing force on the eye based on such contact. Processor 130 may further determine the weight on eye, in relation to the relative distance, by reference to sensed force-distance reference data. The processor may then generate a pictorial representation of the determined weight on eye and transmit the pictorial representation to display 140. System 100 may provide a user with the weight on eye for any detectable position in a range of motion of the suction cone by reference to the sensed force-distance reference data. Further, the measuring device may detect any subsequent detectable position (in time) and generate data relating to that detectable position. Processor 130 may then determine any change in weight on eye in relation to the previously-determined weight on eye. Any such change may be illustrated in the pictorial representation and transmitted to the display, to be presented to the user.

The pictorial representation may indicate the weight on eye in any format, for example, as a number, graph, scale, graphic, dial, or counter. The pictorial representation may indicate a change, such as an increase or decrease in weight on eye, relative position, or detectable position, by presenting a different color, size, or thickness of any aspect of the pictorial representation. The display may include multiple displays and may be a screen, a heads-up display, or a combination.

Processor 130 may be further configured to determine whether the weight on eye is a value that is within a defined acceptable range. The defined acceptable range may be any range chosen by the user and may vary by eye or by patient, according to parameters such as intraocular pressure, curvature of the eye, or any pre-existing conditions of the eye. If the processor determines that the weight on eye is a value within the defined acceptable range, it may be configured to proceed to a standby mode, in which it does not generate a warning. In contrast, the processor may be configured to generate and transmit a warning if it determines that the weight on eye is not a value within the defined acceptable range. The warning may be included in the pictorial representation and may indicate to the user that the weight on eye is not within the defined acceptable range. The warning may further indicate that adjustment of a component of the docking apparatus is necessary to re-enter the acceptable range, in which direction, and to what extent adjustment is required in the Z-direction. Such warning, for example, may be in the form of a colored light, a blinking light, a flashing light, a sound, an alarm, a whistle, a graphic, or any other signal operable to indicate to the user that the weight on eye is not within the defined acceptable range. The warning may be presented to the user in real time, preferably as soon as the processor determines that a warning is necessary. Real time may mean in less than half a second, in less than one second, or otherwise in less than the normal reaction time of a user based on visual information.

As described in FIGS. 2 and 3 below, the sensed-force data referred to by the processor may be generated by incorporating a force sensor into system 100 or a functionally equivalent system. For example, the force sensor may be a weighing device. Although described in detail in FIGS. 2 and 3, the force sensor is operable to sense a sensed force and generate data relating to that sensed force. The processor may be further operable to receive the data, and correlate the sensed force data to a corresponding detectable position. The processor may then determine the weight on eye in relation to any detectable position for which data relating to a sensed force and a detectable position is received.

Further, the sensed force-distance reference data referenced by the processor may include an extrapolated sensed force-distance data set. The extrapolated sensed force-distance data set may be generated by extrapolating previous determinations of weight on eye, corresponding to previously-detected detectable positions. The previous determinations of weight on eye may be extrapolated to include any detectable position or subset thereof within the entire range of motion of the docking apparatus or any component of the docking apparatus, for example, the suction cone. The inclusion of an extrapolated sensed force-distance data set allows the processor to determine a weight on eye for any detectable position within the entire range of motion, without the requirement that actual sensed force-distance reference data be generated or available for those exact detectable positions.

Alternatively, sensed force-distance reference data may be generated that includes a determination of weight on eye in relation to every possible detectable position in the range of motion, such that inclusion or reference to an extrapolated sensed force-distance data set is not necessary. For example, the sensed force-distance reference data may be generated by using a measuring device that is a path recorder operable to detect a detectable position of a component throughout an entire range of motion.

Sensed force-distance reference data and/or an extrapolated sensed force-distance data set may be generated by system 100 or any functionally identical system. Such sensed force-distance reference data may then be included in memory 135 or the memory of any other functionally identical system, and referred to by processor 130 or the processor of any other functionally identical system. By reference to such sensed force-distance reference data, system 100 may generate an indirect determination of weight on eye for any detectable position in the entire range of motion of the docking apparatus or a component thereof.

Processor 130 may comprise, for example a microprocessor, microcontroller, digital signal processor (DSP), application specific integrated circuit (ASIC), or any other digital or analog circuitry configured to interpret and/or execute program instructions and/or process data. In some embodiments, processor 130 may interpret and/or execute program instructions and/or process data stored in a memory. The memory may be configured in part or whole as application memory, system memory, or both. The memory may include any system, device, or apparatus configured to hold and/or house one or more memory modules. Each memory module may include any system, device or apparatus configured to retain program instructions and/or data for a period of time (e.g., computer-readable media). The various servers, electronic devices, or other machines described may contain one or more similar such processors or memories for storing and executing program instructions for carrying out the functionality of the associated machine.

Figure 2:
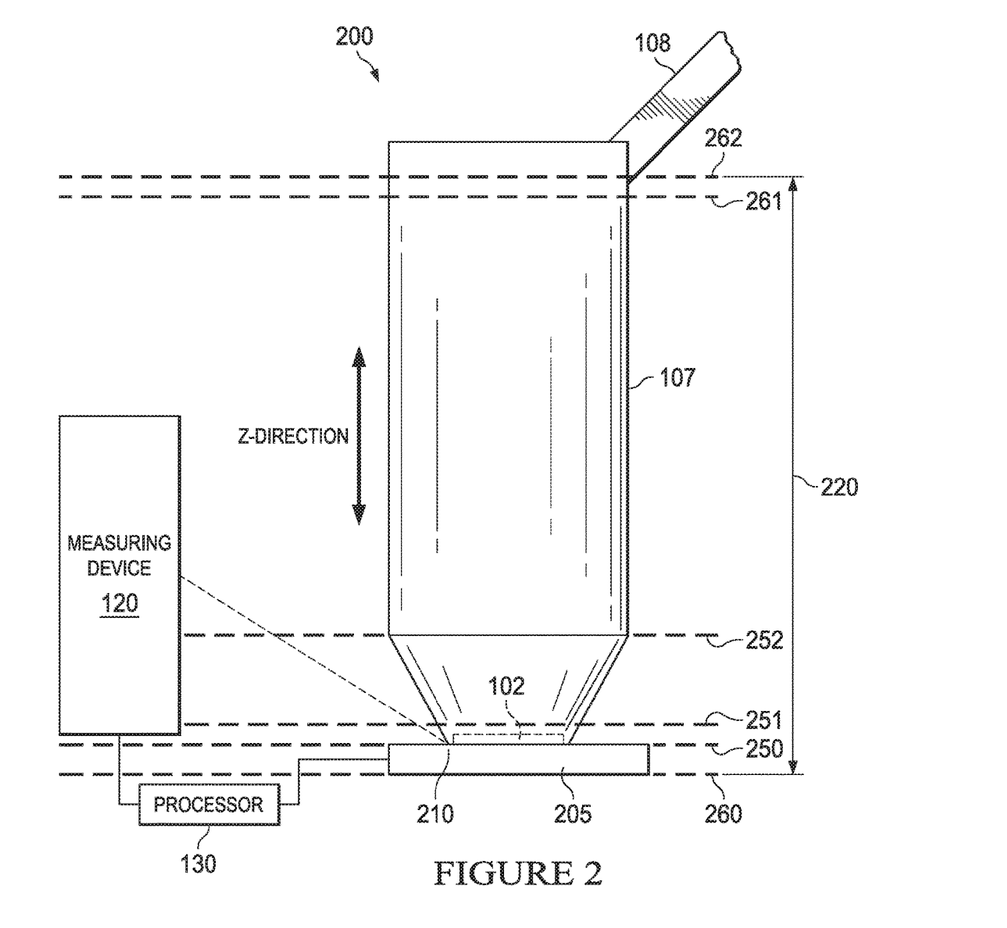
FIG. 2 is a schematic representation of generating sensed force-distance reference data by incorporating a force sensor into the system or a functionally identical system.

FIG. 2 is a schematic representation 200 of generating sensed force-distance reference data by incorporating a force sensor into the system shown in FIG. 1 or a functionally identical system. The components of the system of FIG. 1, as illustrated in FIG. 2, are suction cone 107, connected to control device 108, lens 102, measuring device 120, and processor 130. In this example, target detectable position 210 is a position toward the bottom of the suction cone that is equivalent in the Z-direction to the position of lens 102 in the Z-direction. Lens 102 is contained within suction cone 107. The system shown further includes force sensor 205, which has been incorporated into the system of FIG. 1. Scale 220 indicates the entire range of motion of the suction cone, which is a component of the docking apparatus.

Measuring device 120 is operable to detect detectable position 210 of suction cone 107 and generate data relating to the detectable position. Force sensor 205 is operable to sense a sensed force and generate data relating to the sensed forced. Processor 130 is operable to receive data from the measuring device and the force sensor, and determine a relative distance between the detectable position in relation to a defined "neutral position." The "neutral position" defined by the user indicates a neutral position of the eye, which is a position in which the eye would be in contact with the suction cone, with a substantially neutral pulling or pushing force on the eye based on the contact. Processor 130 may correlate the relative distance to the sensed force corresponding to a weight on eye, to generate sensed force-distance reference data for that detectable position.

In this example, measuring device 120 and force sensor 205 generate and transmit data relating to detectable positions 250, 251, and 252. Processor 130 may determine a relative distance between each of these detectable positions and the defined neutral position and correlate each respective relative distance to the corresponding weight on eye. Thus, for example, if suction cone 107 is later-adjusted to detectable position 252, processor 130 may determine the weight on eye by reference to the sensed force-distance reference data previously generated. Accordingly, the processor may determine the weight on eye for any detectable position within a range of motion, at least by reference to sensed force-distance reference data relating to detectable positions previously generated.

In one example, the measuring device may be a path recorder operable to detect a detectable position of the suction cone as it is adjusted throughout its entire range of motion. Force sensor data may be generated in any increment throughout this range. Such data may be processed to generate sensed force-distance reference data for any detectable position in the entire range of motion of the suction cone. Thus, the processor may subsequently determine weight on eye by reference to sensed force-distance reference data for any subsequently-detected detectable position. Such sensed force-distance reference data, once generated, may be included in the memory of the system shown in FIG. 1 or any functionally identical system.

As another example, if sensed force-distance reference data relating to every detectable position in the entire range of motion is not generated, then the processor may determine a weight on eye for any detectable position by reference to an extrapolated sensed force-distance data set that may be included in the sensed force-distance reference data. In this example, data of weight on eye relating to detectable positions 250, 251, and 252 may be extrapolated across the entire range of motion of the suction cone. Extrapolated data points 260, 261, and 262 illustrate detectable positions for which extrapolated sensed force-distance data may be generated from actual detected positions 250, 251, and 252. For example, extrapolated data point 260 indicates the lowest point (in the Z-direction) of the range of motion and extrapolated data point 262 indicates the highest point (in the Z-direction) of the range of motion. Such data may be extrapolated in any increment. Once extrapolated, an extrapolated sensed force-distance data set is generated, which may be included in the sensed force-distance reference data referred to by the processor. Thus, the processor may determine the weight on eye for any detectable position in the entire range of motion by reference to sensed force-distance reference data, which may further include an extrapolated sensed force-distance data set.

Figure 3:
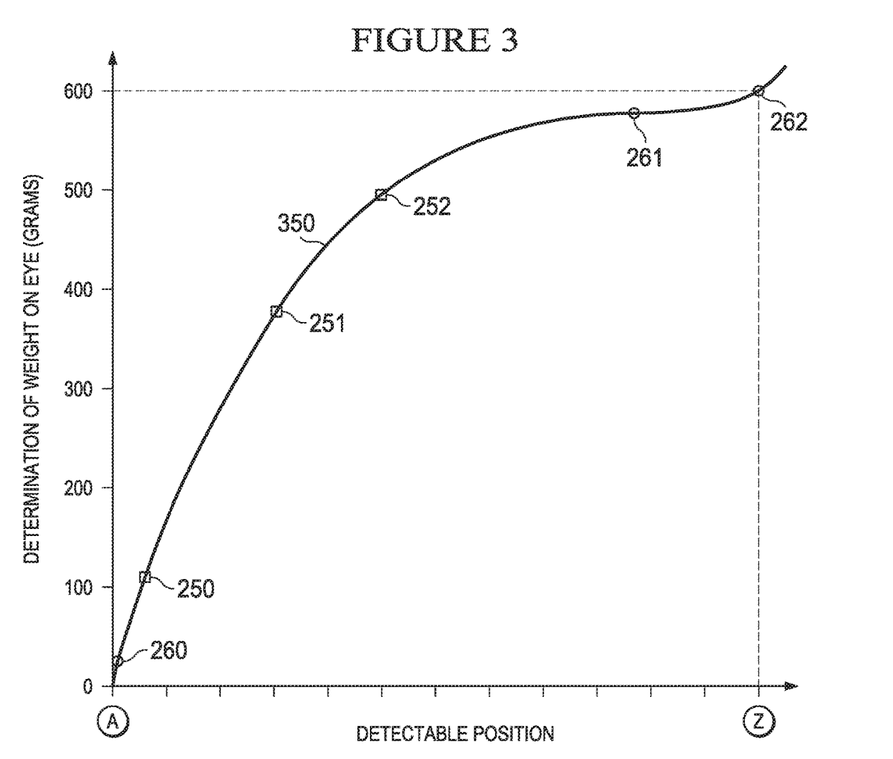
FIG. 3 a graph illustrating an extrapolation of weight on eye, in relation to detectable positions of the suction cone, within a range of motion of the suction cone.

FIG. 3 a graph illustrating an extrapolation of weight on eye, in relation to detectable positions of the suction cone, within a range of motion of the suction cone. The graph of FIG. 3 has an X-axis of detectable positions of the suction cone, where "A" indicates the lowest detectable position (in the Z-direction) of the range of motion of the suction cone and "Z" indicates the highest detectable position (in the Z-direction) of that range of motion. The Y-axis illustrates determinations of weight on eye in grams, although any metric or scale of weight may be used. Detectable positions 250, 251, and 252 correspond to the detectable positions actually measured, as described in FIG. 2. Likewise, extrapolated data points 260, 261, and 262 correspond to the extrapolated data, as described in FIG. 2. Extrapolated line 350 indicates a determination of weight on eye in grams for any detectable position in the entire range of motion. Thus, extrapolated line 350 illustrates an extrapolated sensed force-distance reference data set that may be included in the sensed force-distance reference data referred to by the processor. Any or all of the extrapolated data illustrated by extrapolated line 350 may be included in the sensed force-distance reference data.

Figure 4:
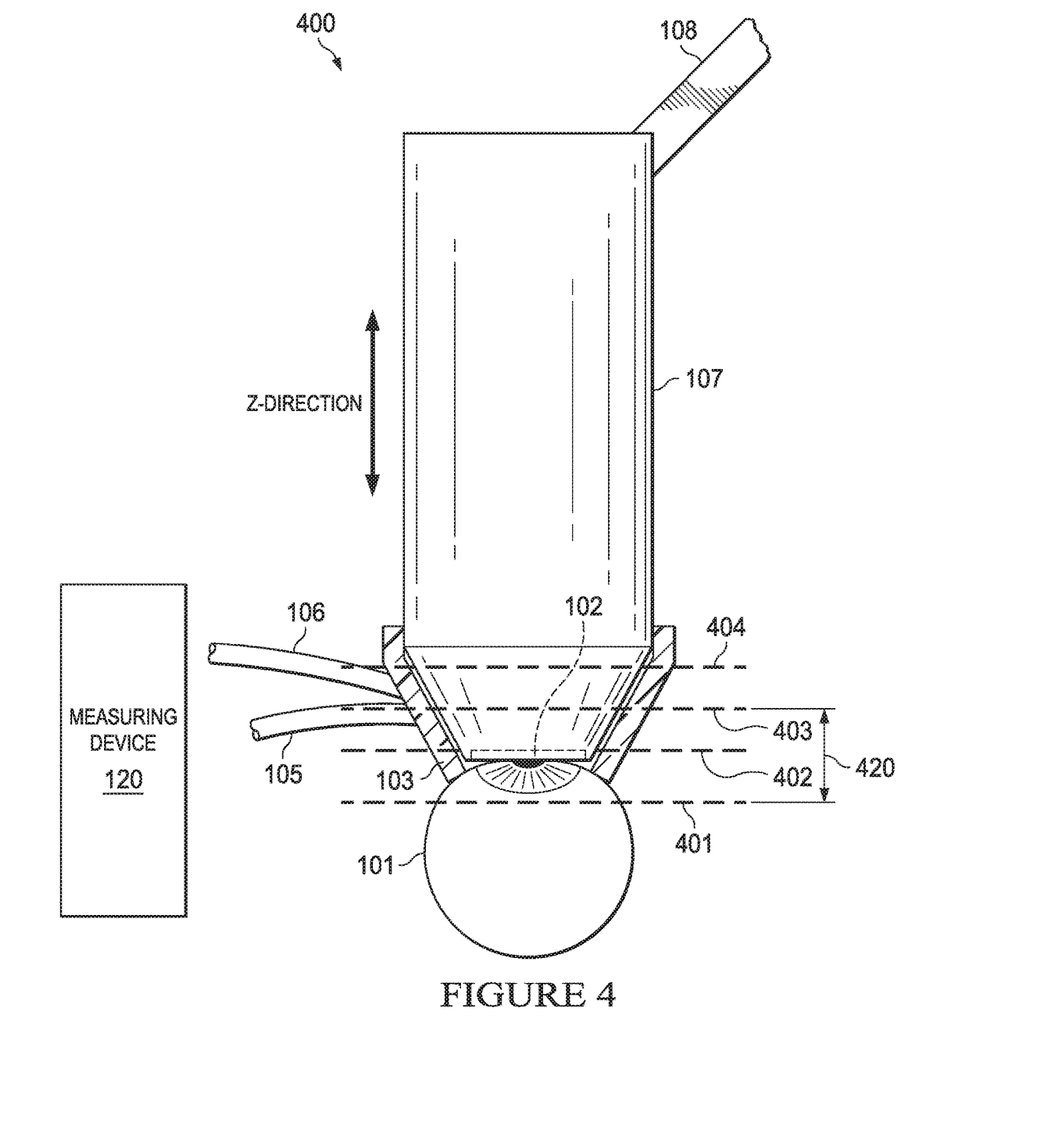
FIG. 4 is a schematic representation of a system for indirectly determining weight on eye during laser ophthalmic surgery, in typical user operation.

FIG. 4 is a schematic representation 400 of a system for indirectly determining weight on eye during laser ophthalmic surgery, in typical user operation. As shown, the system is in a docked state, as indicated by contact between eye 101 and lens 102, suction cone 107, and suction ring 103. Suction is applied by vacuums 105 and 106. In the docked position shown, measuring device 120 may detect any detectable position within a range of motion of the suction cone, for example, detectable positions 401, 402, 403, or 404. As illustrated in FIG. 4, detectable position 402 indicates the current docked position. The system may determine the weight on eye at detectable position 402 as described in FIG. 1. In the event that the suction cone is adjusted or the eye moves during docking or during the procedure to positions 401, 403, or 404, for example, measuring device 120 is operable to detect the new detectable position. The system may then determine the new weight on eye, generate a pictorial representation of weight on eye, and transmit the pictorial representation to a display to be presented to a user.

As shown in FIG. 4, scale 420 indicates an acceptable range defined by the user. The acceptable range may vary based on patient-specific parameters such as intraocular pressure, curvature of the eye, or any pre-existing conditions of the eye. In this example, at detectable position 402, the system will not generate or transmit a warning because detectable position 402 is within acceptable range 420. In contrast, at detectable position 404, the system will generate and transmit a warning because detectable position 404 is outside of acceptable range 420. The warning may be included in the pictorial representation presented by the display. The warning may further indicate that adjustment of a component of the docking apparatus is necessary, in which direction, and to what extent adjustment is necessary in the Z-direction. For example, the warning generated at detectable position 404 may indicate that the detectable position is not within the acceptable range, the suction cone must be adjusted downward to re-enter the acceptable range, and that the suction cone must be adjusted by the difference in distance between detectable positions 402 and 404.

Figure 5:
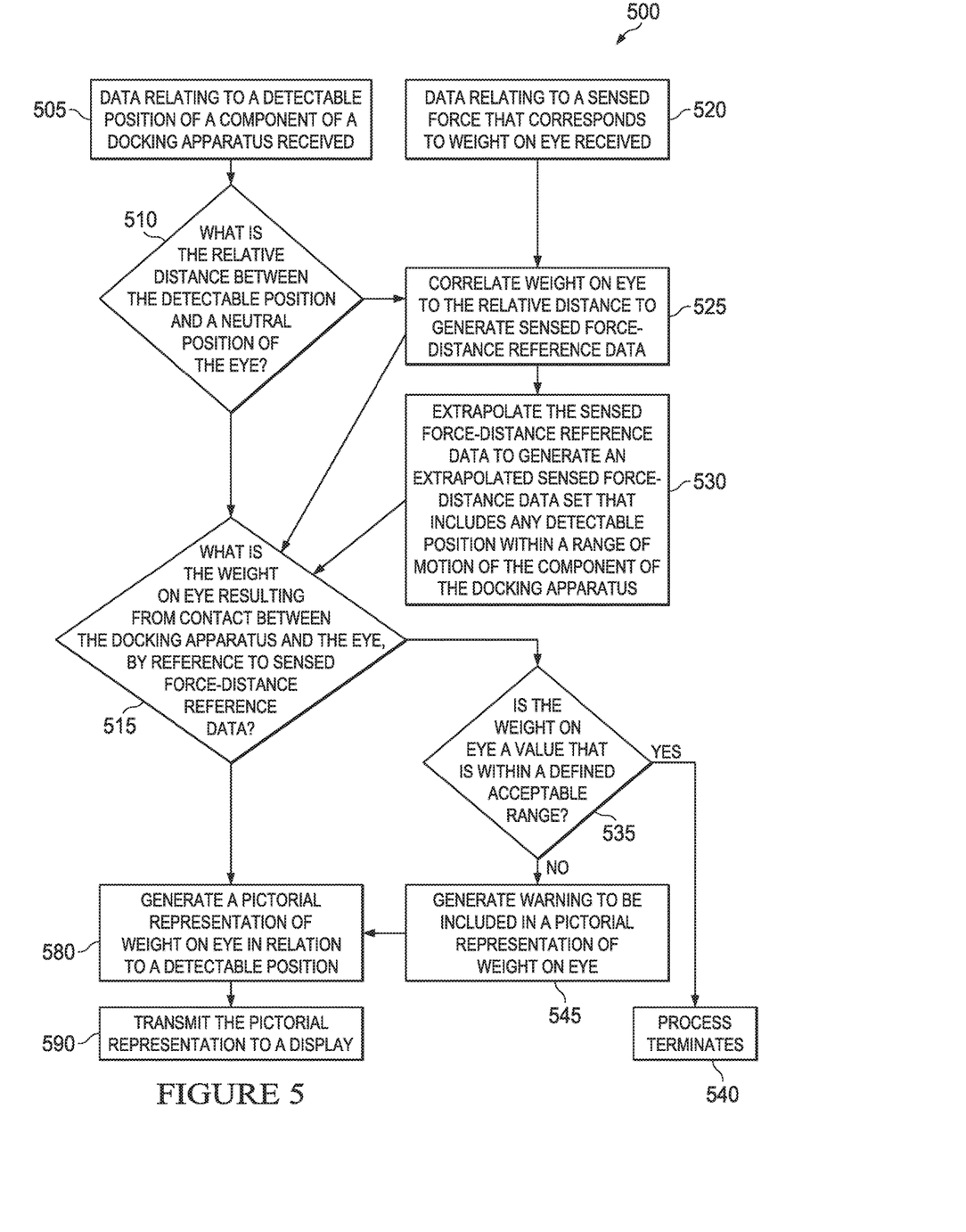
FIG. 5 is a flow chart of a method for indirectly determining weight on eye during laser ophthalmic surgery.

FIG. 5 is a flow chart of a method for indirectly determining weight on eye during laser ophthalmic surgery. At step 505, data relating to a detectable position of a component of a docking apparatus is received, the docking apparatus used in ophthalmic laser surgery. At step 510, the relative distance between the detectable position and a neutral position of the eye may be determined. A neutral position of the eye is a position in which the eye is in contact with the component (of the docking apparatus), with a substantially neutral pulling or pushing force on the eye based on the contact. At step 515, the weight on eye is determined, the weight resulting from contact between the docking apparatus and the eye by reference to sensed force-distance reference data. Sensed force-distance reference data refers to data relating a relative distance (between a detectable position and a neutral position of the eye) and a weight on eye. Such sensed force-distance reference data may include only data actually generated, or the sensed force-distance reference data may further include an extrapolated sensed force-distance data set. Thus, weight on eye may be determined at step 515 by reference to sensed force-distance reference data that may or may not include an extrapolated sensed force-distance data set. Reference data is typically not generated during the actual ophthalmic surgery. Rather, it is typically generated for a surgical system including at least the system described herein as well as a particular femtosecond laser and other set parts that may contribute to weight on eye. The reference data is then provided with similar systems for use during ophthalmic surgery. Such reference data may be generated during development of a given surgical system and occasionally checked using newly manufactured systems. It is also possible for the reference data to be specific for each individual surgical system. It may then be generated after manufacturing is complete or after the system has been installed. A technician may periodically check and update the reference data for particular systems.

After weight on eye is determined at step 515, at step 580, a pictorial representation of weight on eye in relation to the detectable position may be generated, and at step 590, the pictorial representation may be transmitted to a display.

Alternatively, after the weight on eye is determined at step 515, at step 535, whether the weight on eye is a value that is within a defined acceptable range may be determined. If, at step 535, the weight on eye is determined to be within the acceptable range, than at step 540, the process terminates because no warning must be generated indicating that the weight on eye is not within the acceptable range. In contrast, if at step 535, a value of weight on eye is determined not to be within the acceptable range, than at step 545, a warning may be generated to be included in a pictorial representation of weight on eye. Such warning, for example, may be in the form of a colored light, a blinking light, a flashing light, a sound, an alarm, a whistle, a graphic, or any other signal operable to indicate to the user that the weight on eye is not within the defined acceptable range. The warning may be presented to the user in real time, preferably as soon as the processor determines that a warning is necessary. Real time may mean in less than half a second, in less than one second, or otherwise in less than the normal reaction time of a user based on visual information. At step 580, the pictorial representation of weight on eye in relation to a detectable position may be generated, and at step 590, the pictorial representation may be transmitted to a display.

The pictorial representation may indicate the weight on eye in any format, for example, as a number, graph, scale, graphic, dial, or counter. The pictorial representation may indicate a change, such as an increase or decrease in weight on eye, relative position, or detectable position, by presenting a different color, size, or thickness of any aspect of the pictorial representation. The display may include multiple displays and may be a screen, a heads-up display, or a combination.

If the sensed force-distance reference data is to include an extrapolated sensed force-distance data set, at step 520, data relating to a sensed force that corresponds to a weight on eye may be received, at step 505, data relating to a detectable position of a component of a docking apparatus may be received, and at step 510, the relative distance between the detectable position and a neutral position of the eye may be determined. At step 525, the weight on eye may be correlated to a relative distance that corresponds to a detectable position, to generate sensed force-distance reference data. Such sensed force-distance reference data may be extrapolated, at step 530, to generate an extrapolated sensed force-distance data set. The extrapolated sensed force-distance data set may include any detectable position within the entire range of motion, and the data set may be included in the sensed force-distance reference data referred to for determinations of weight on eye. Accordingly, by reference to the sensed force-distance reference data, weight on eye may be indirectly determined, at step 515, for any detectable position within the entire range of motion of the component.

The above disclosed subject matter is to be considered illustrative, and not restrictive, and the appended claims are intended to cover all such modifications, enhancements, and other embodiments which fall within the true spirit and scope of the present disclosure. Thus, to the maximum extent allowed by law, the scope of the present disclosure is to be determined by the broadest permissible interpretation of the following claims and their equivalents, and shall not be restricted or limited by the foregoing detailed description.

The invention claimed is:

1. A system for indirectly determining weight on eye, comprising:
   a measuring device operable to detect a detectable position of a component of a docking apparatus and generate data relating to the detectable position;
   a display; and
   a processor operable to:
      receive data from the measuring device relating to the detectable position;
      determine a relative distance between the detectable position of the component in relation to a neutral position of the eye;
      determine weight on eye resulting from contact between the docking apparatus and the eye by reference to sensed force-distance reference data;
      generate a pictorial representation of the weight on the in eye in relation to the detectable position; and
      transmit the pictorial representation to the display, wherein the sensed force-distance reference data is generated by:
   incorporating a force sensor into the system or a functionally identical system, the force sensor operable to sense a sensed force and generate data relating to the sensed forced that corresponds to weight on eye;
   receiving at the processor, data from the force sensor and the measuring device; and
   correlating weight on eye to the relative distance to generate the sensed force-distance reference data.

2. The system of claim 1, wherein the weight on eye is determined by extrapolating the sensed force-distance reference data.

3. The system of claim 2, wherein the sensed force-distance reference data is extrapolated to include any detectable position in an entire range of motion of the component, or any subset thereof.

4. The system of claim 1, wherein components of the docking apparatus include a suction cone, a suction ring, and a lens.

5. The system of claim 4, wherein the measuring device is operable to detect a detectable position of the suction cone by using light barriers.

6. The system of claim 4, wherein the measuring device is operable to detect a detectable position of the suction cone by using switches.

7. The system of claim 4, wherein the measuring device is operable to detect a detectable position of the suction cone by using a path recorder.

8. The system of claim 4, wherein the measuring device is operable to detect a detectable position of the suction cone by using an eye camera, multiple eye cameras, or an eye tracking system.

9. The system of claim 1, wherein the neutral position of the eye is a position in which the eye is in contact with the component, with a substantially neutral pulling or pushing force on the eye based on the contact.

10. The system of claim 1, wherein the force sensor is a weighing device.

11. The system of claim 1, wherein the processor is further configured to generate a warning and transmit the warning to the display, the warning indicating that the weight on eye is outside of a defined acceptable range.

12. The system of claim 11, wherein the warning further indicates that adjustment of the component of the docking apparatus is necessary, the direction the component must be adjusted to remain in the defined acceptable range, the extent to which the component must be adjusted in the Z-direction, or any combination thereof.

13. A method for indirectly determining weight on eye, comprising:

receiving data from a measuring device relating to a detectable position of a component of a docking apparatus;

determining a relative distance between the detectable position of the component in relation to a neutral position of the eye;

determining the weight on eye resulting from contact between the docking apparatus and the eye by reference to sensed force-distance reference data;

generating a pictorial representation of weight on the in eye in relation to the detectable position; and transmitting the pictorial representation to a display, wherein the sensed force-distance reference data is generated by:

receiving at the processor data relating to the sensed forced that corresponds to weight on eye and data relating to a detectable position; and correlating weight on eye to the relative distance to generate the sensed force-distance reference data.

14. The method of claim 13, wherein the weight on eye is determined by extrapolating the sensed force-distance reference data.

15. The method of claim 14, wherein the sensed force-distance reference data is extrapolated to include any detectable position within an entire range of motion of the component, or any subset thereof.

16. The method of claim 13, wherein the neutral position of the eye is a position in which the eye is in contact with the component, with a substantially neutral pulling or pushing force on the eye based on the contact.

17. The method of claim 13, wherein determining the weight on eye by reference to sensed force-distance reference data further includes generating and transmitting a warning, the warning indicating that the weight on eye is outside of a defined weight measurement range.

18. The method of claim 17, wherein the warning further indicates that adjustment of the component of the docking apparatus is necessary, the direction the component must be adjusted to remain in the defined acceptable range, the extent to which the component must be adjusted in the Z-direction, or any combination thereof.

* * * * *